US009402713B2

(12) United States Patent
Keller et al.

(10) Patent No.: US 9,402,713 B2
(45) Date of Patent: **\*Aug. 2, 2016**

(54) APPARATUS AND PROCESS FOR DELIVERING A SILICONE PROSTHESIS INTO A SURGICAL POCKET

(71) Applicant: KELLER MEDICAL, INC., Stuart, FL (US)

(72) Inventors: Kevin Keller, Greenville, SC (US); Judy Jones Senn, Spartanburg, SC (US)

(73) Assignee: KELLER MEDICAL, INC., Stuart, FL (US)

( * ) Notice: Subject to any disclaimer, the term of this patent is extended or adjusted under 35 U.S.C. 154(b) by 324 days.

This patent is subject to a terminal disclaimer.

(21) Appl. No.: 13/802,332

(22) Filed: Mar. 13, 2013

(65) Prior Publication Data

US 2014/0074235 A1    Mar. 13, 2014

Related U.S. Application Data

(63) Continuation of application No. 13/365,065, filed on Feb. 2, 2012, now Pat. No. 8,555,893, which is a continuation of application No. 12/228,072, filed on Dec. 7, 2007, now Pat. No. 8,211,173.

(51) Int. Cl.
*A61F 2/12*     (2006.01)

(52) U.S. Cl.
CPC ........................................ *A61F 2/12* (2013.01)

(58) Field of Classification Search
CPC ....................................................... A61F 2/12
USPC ................... 623/7, 8; 128/898; 604/48, 93.01, 604/94.01, 181, 183–186, 288.1
See application file for complete search history.

(56) References Cited

U.S. PATENT DOCUMENTS

| | | | |
|---|---|---|---|
| 2,935,241 A | | 5/1960 | Brady |
| 3,138,821 A | | 6/1964 | Macciocchi et al. |
| 3,156,240 A | | 11/1964 | Harrison et al. |
| 3,883,902 A | | 5/1975 | Lynch |
| 4,035,850 A | | 7/1977 | Cresswall |
| 4,650,833 A | | 3/1987 | Sakagami et al. |
| 4,955,906 A | | 9/1990 | Coggins et al. |
| 5,052,554 A | * | 10/1991 | Leonard ............... A61C 9/0026 206/219 |
| 5,201,779 A | | 4/1993 | Shiao |
| 5,500,019 A | | 3/1996 | Johnson et al. |
| 5,571,178 A | | 11/1996 | Ledergerber |
| 5,723,006 A | | 3/1998 | Ledergerber |
| 6,238,799 B1 | | 5/2001 | Opolski |

(Continued)

FOREIGN PATENT DOCUMENTS

CN        201076483       6/2008
FR        2 733 903 A1    11/1996

OTHER PUBLICATIONS

Feb. 28, 2012 Letter from Pearne & Gordon re Ledergerber U.S. Pat. No. 5,723,006.
Feb. 28, 2012 Claim Chart regarding Ledergerber U.S. Pat. No. 5,723,006.
Allergan, Delivery Assistance Sleeve, Directions for Use, Jul. 12, 2011.

(Continued)

*Primary Examiner* — Ahmed Farah
(74) *Attorney, Agent, or Firm* — ONE LLP

(57) ABSTRACT

A tapered sleeve is provided that includes a lubricating coating on an inner surface. An implant (e.g., a pre-filled silicon breast implant) is introduced into a large end of the sleeve and extruded into a surgical pocket of minimal access incision size through a small-sized end of the apparatus.

21 Claims, 3 Drawing Sheets

(56) References Cited

U.S. PATENT DOCUMENTS

| | | | |
|---|---|---|---|
| 6,383,191 | B1 | 5/2002 | Zdeblick et al. |
| 6,520,989 | B1 | 2/2003 | Eaton |
| 6,743,523 | B1 | 6/2004 | Woo et al. |
| 6,866,936 | B2 | 3/2005 | Opolski |
| 7,137,995 | B2 | 11/2006 | Studin |
| 7,267,885 | B1 | 9/2007 | Woo et al. |
| 7,775,716 | B2 * | 8/2010 | Ejeblad ............... A23G 3/28 383/105 |
| 8,206,443 | B2 * | 6/2012 | Preissman ............. A61F 2/12 623/7 |
| 8,211,173 | B2 * | 7/2012 | Keller et al. ................ 623/7 |
| 2003/0199726 | A1 * | 10/2003 | Gatto ............... A61N 5/1027 600/3 |
| 2006/0184100 | A1 | 8/2006 | Studin |
| 2007/0038310 | A1 | 2/2007 | Guetty |
| 2007/0276484 | A1 * | 11/2007 | Abell ................. A61F 2/12 623/7 |
| 2008/0241212 | A1 | 10/2008 | Moses et al. |
| 2009/0099588 | A1 | 4/2009 | Makower et al. |
| 2009/0204107 | A1 | 8/2009 | Keller et al. |
| 2010/0030256 | A1 * | 2/2010 | Dubrul ............ A61B 10/0266 606/200 |
| 2010/0222802 | A1 | 9/2010 | Gillespie, Jr. et al. |
| 2010/0280610 | A1 | 11/2010 | Preissman |
| 2011/0035003 | A1 | 2/2011 | Preissman |
| 2011/0082546 | A1 | 4/2011 | Freund |
| 2015/0032208 | A1 * | 1/2015 | Preissman ............. A61F 2/12 623/8 |

OTHER PUBLICATIONS

Mladick, R., "No-Touch" Submascular Saline Breast Augmentation Technique, Aesth. Plast. Surg. 17:183-192, 1993.
Mladick No-Touch Sleeve, *Finesse in Breast Augmentation*, 2000 Byron Medical.
09844125.6, EP, Search Report, Jun. 9, 2012.
PCT/US2009/002592, International Search Report, Nov. 10, 2011.
PCT/US2012/024917, Written Opinion, Nov. 22, 2012.
U.S. Appl. No. 13/365,065, US, Office Action, Oct. 23, 2012.
U.S. Appl. No. 13/372,196, US, Office Action, Oct. 24, 2012.
WO, PCT/US2009/002592 ISR, Jun. 26, 2009.
WO, PCT/US2009/002592 IPRP, Nov. 1, 2011.
WO, PCT/US2012/024917 ISR, Nov. 22, 2012.
WO, PCT/US2012/024917 IPRP, Aug. 19, 2014.
Bell, M., et al., "An illuminating no-touch device for breast augmentation," Can J. Plast. Surg, vol. 17, No. 1, pp. 30-31.
Hilton, Lisette, "Plastic Surgeons reveal reality of global hot topics in cosmetic surgery", Cosmetic Surgery Times, Aug. 1, 2011, retrieved from http://cosmeticsurgerytimes.modernmedicine.com/cosmetic-surgery-times/news/modernmedicine/modern-medicine-feature-articles/plastic-surgeons-reveal-?page=full.
Moyer, H.R., et al, "Sterility in Breast Implant Placement: The [Keller Funnel] and the No Touch Technique", Plastic & Reconstructive Surgery, vol. 128, No. 4, Oct. 2011, p. 9.
Survey Report: Keller Funnel Opinion Survey, WISERInsights, Miami, FL, Nov. 2010, retrieved from http://questionpro.com/a/summaryReport.do?surveyID=1872971.

* cited by examiner

APPARATUS AND PROCESS FOR DELIVERING A SILICONE PROSTHESIS INTO A SURGICAL POCKET

RELATED APPLICATION

This application is a continuation of U.S. patent application Ser. No. 13/365,065, filed Feb. 2, 2012, which is a continuation of U.S. patent application Ser. No. 12/228,072 now U.S. Pat. No. 8,211,173, filed Dec. 7, 2007, each of which is incorporated herein by reference in its entirety. Non provisional patent application Ser. No. 12/228,072 is a conversion of Provisional Application Ser. No. 61/005,777, filed Dec. 7, 2007, done by way of petition under 37 CFR 1.53(c)(3) granted on Feb. 19, 2009. The present application claims the benefit of the Dec. 7, 2007 filing date.

FIELD OF INVENTION

This invention is directed to a delivery apparatus for facilitating the insertion of a silicone implant, such as a breast prosthesis, into a surgically developed pocket.

BACKGROUND OF THE INVENTION

This invention relates to the placement of silicone implants within a patient's body. Silicone implants have been in worldwide use for a number of years. While marketing of the implants was halted within the United States for over 15 years, the use of silicone implants has resumed within the United States. One problem with silicone implants is that the implants are provided in a filled condition and must be inserted into a surgical pocket. As a result, traditional surgical approaches require the use of larger incisions in comparison to saline implants which can be inserted through small incisions which are later filled in situ with saline.

While many patients prefer the more natural qualities of silicone, patients remain apprehensive because of the larger incisions and possibility for visible scars which result from silicone implants.

An additional concern with the use of silicone implants is that the longevity and integrity of the implants can be compromised by the conventional insertion process. A typical insertion process involves hand manipulation by the surgeon of the implant in order to insert it into the surgical pocket. Studies have shown that implant failures are often associated with an area of minor damage to the outer surface of the implant. The damaged areas are believed to correlate to excessive pressure applied by hand manipulation of the implant and/or damage associated with a "nick" of the implant surface by a "touching" injury such as a fingernail or insertion that damages the implant.

An additional consideration with respect to silicone implants involves the amount of time required to insert the implants. A traditional hand manipulation of an implant into a surgical pocket can take between 10 to 20 minutes per implant for even a highly skilled surgical practitioner. Typically, hand manipulation of an implant requires the use of a larger incision and would be done with a saline implant. The amount of time required has a direct bearing on the expense of the procedure, the surgical expense reflecting the surgeon's time, the support staff within the operating room, and the amount of time allocated for the surgical procedure. Accordingly, any improvements to reduce the time required for implantation of the silicone implant will have significant cost savings with respect to the surgical procedure.

Accordingly, there remains room for improvement and variation within the art.

SUMMARY OF THE INVENTION

It is one aspect of at least one of the present embodiments to provide an apparatus and a process for facilitating the delivery of a silicone implant into a surgically developed pocket.

It is a further aspect of at least one embodiment of the present invention to provide for an apparatus and process for facilitating the placement of a filled silicone implant into a surgical pocket through a surgical incision that is too small for a manual insertion of an implant.

It is a further aspect of at least one of the present embodiments to provide for an apparatus and process that allows insertion of a silicone implant through a sleeve defining a small diameter outlet into a patient without direct hand manipulation of the implant.

It is yet a further and more particular aspect of at least one aspect of at least one of the present embodiments to provide for a process and apparatus that allows for a "touchless" insertion of a silicone implant into a surgical pocket.

These and other features, aspects, and advantages of the present invention will become better understood with reference to the following description and appended claims.

BRIEF DESCRIPTION OF THE DRAWINGS

A fully enabling disclosure of the present invention, including the best mode thereof to one of ordinary skill in the art, is set forth more particularly in the remainder of the specification, including reference to the accompanying drawings.

DESCRIPTION OF THE PREFERRED EMBODIMENT

Reference will now be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used on another embodiment to yield a still further embodiment. Thus, it is intended that the present invention cover such modifications and variations as come within the scope of the appended claims and their equivalents. Other objects, features, and aspects of the present invention are disclosed in the following detailed description. It is to be understood by one of ordinary skill in the art that the present discussion is a description of exemplary embodiments only and is not intended as limiting the broader aspects of the present invention, which broader aspects are embodied in the exemplary constructions.

In describing the various figures herein, the same reference numbers are used throughout to describe the same material, apparatus, or process pathway. To avoid redundancy, detailed descriptions of much of the apparatus once described in relation to a figure is not repeated in the descriptions of subsequent figures, although such apparatus or process is labeled with the same reference numbers.

Figure 1:
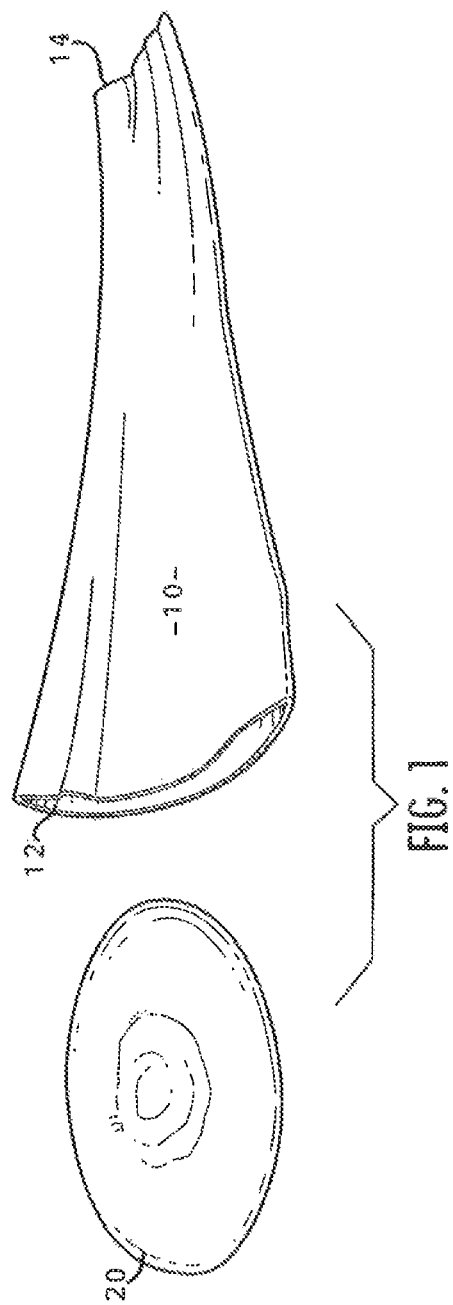
FIG. 1 is a perspective view of a prosthetic insertion sleeve along with a silicone prosthesis.
Figure 2:
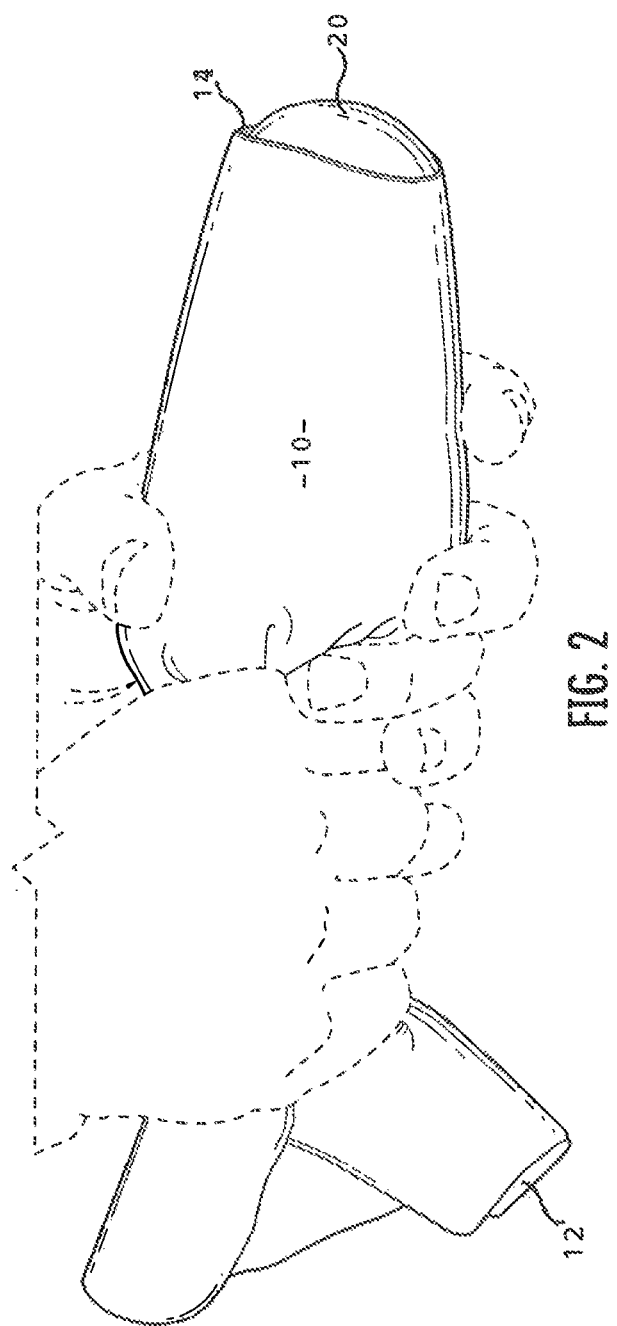
FIG. 2 is a picture of the insertion sleeve with the silicone implant positioned within the sleeve and showing further hand manipulation of the implant via the sleeve.
Figure 3:
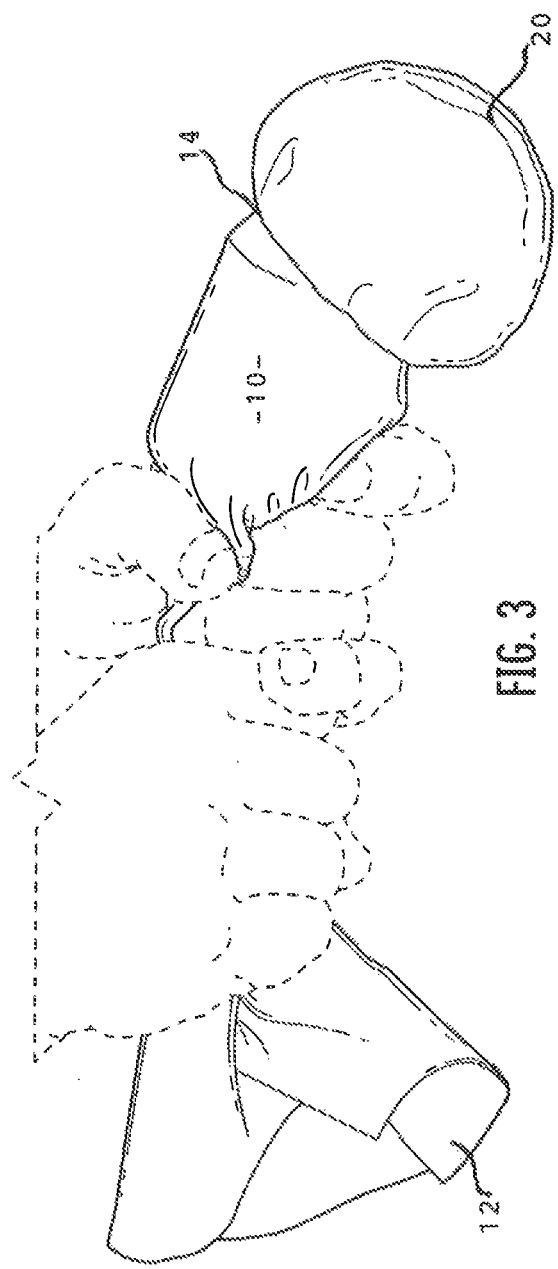
FIG. 3 is a view similar to FIG. 2 showing additional manipulation of the prosthesis through the sleeve and illustrating a portion of the prosthesis exiting a tapered end of the sleeve.

As seen in reference to FIGS. 1-3, a sleeve 10 is provided having a general conical shape and which defines a first opening 12 at a larger end of the sleeve and a smaller opening 14 along the tapered terminal tip of sleeve 10. As best seen in reference to FIG. 1, sleeve 10 may be provided by a material which is sufficiently flexible and which enables the sleeve 10 to assume a flattened configuration for storage and shipping.

As seen in reference to FIGS. 2 and 3, when an implant 20, such as a silicone implant, is placed through opening 12 into the interior of sleeve 10, sleeve 10 can be manipulated to conform to the shape of the implant 20 as well as to apply pressure to direct the implant 20 along the length of the sleeve and toward opening 14.

Preferably, sleeve 10 is of a flexible material. In one embodiment of the invention, sleeve 10 can be provided by a fabric material such as a plastic-containing fabric which is pliable yet resistant to stretching. It is also envisioned that use of a transparent plastic or other suitable polymer material which has sufficient properties including flexibility and non-elasticity may be used. It is believed that there are advantages to using a transparent or semi-transparent material to assist the surgeon in proper orientation of the implant 20 within the interior of sleeve 10. Suitable transparent materials may include Mylar.RTM., plastics made from Tygon.RTM. brand of plastics, vinyls, polyvinyl chloride, and other similar materials.

One suitable material which is flexible and transparent includes compositions of ethylene and alpha-olefin copolymers such as the compositions used in IV saline bags. Suitable multilayer films and sealed structures are taught in U.S. Pat. Nos. 6,743,523 and 7,267,885 both assigned to Baxter International Inc., and which are incorporated herein by reference. As disclosed therein, suitable films heat sealed to form suitable containers, are transparent with minimal hazing, and can be sterilized using gas sterilization or heat with intact seals and remain sufficiently flexible and pliable for the necessary manipulation described herein.

Other attributes of sleeve 10 include the ability to provide sleeve 10 as a sterile component. Accordingly, the material must be capable of withstanding at least one of several conventional sterilization techniques such as a steam autoclave, chemical gas sterilization, or irradiation. Additionally, the interior surface of sleeve 10 may preferably have a low coefficient of friction to facilitate passage of the implant 20 through the sleeve 10. It has been found that using a surgically appropriate lubricant will facilitate passage of the implant 20 through the interior of sleeve 10. Such lubricants may be applied directly to the implant 20 or the sleeve can be coated with lubricant or supplied pre-coated with a lubricant that is already present within sleeve 10.

Since the size of silicone implants 20 may vary in a range from about 150 cc to about 800 cc, the dimensions of opening 14 may be varied to accommodate various size implants 20. Preferably, sleeve 10 is provided with an opening 14 sized to fit the smallest implant. The tip opening 14 may be enlarged by cutting portions of the sleeve to provide a larger opening. If desired, indicia may be present on the exterior of sleeve 10 to allow the cutting of the sleeve to the proper dimensions for the size of the implant 20.

Alternatively, the tip opening 14 can have a diameter sized to allow the largest standard implant of 800 cc to exit the sleeve. According to this invention, it has been found that an opening 14 having a diameter of about 6 cm will allow delivery of the implant into the surgical pocket. As described below, use of an optional tip would allow for a sleeve to be provided having a single opening size to accommodate the largest implant. Selection of an appropriate tip can then be made based upon the size of the implant.

While it is believed preferable that sleeve 10 be provided from a single structural substrate, it is also recognized that an equivalent device can be provided of a flexible sleeve 10 having a separate inner liner (not illustrated) which may be present within the interior of sleeve 10. The liner could either be integral with sleeve 10 or may be a separate layer of material manually inserted within the interior of sleeve 10 at the time of use.

The larger opening 12 of sleeve 10 allows the implant to be placed within the sleeve with little force or manual manipulation. When the implant is within the interior of sleeve 10, the larger opening may be twisted closed as seen in FIGS. 2 and 3. Thereafter, the surgeon is able to apply manual pressure via the sleeve to the implant 20. The surgeon is thus able to apply pressure to the implant, forcing the implant toward the smaller opening 14. As seen in reference to FIGS. 2 and 3, the implant can be forced through the small opening 14.

As the surgeon is manipulating the implant through sleeve 10, the opening 14 is placed within the surgical pocket designed for receiving the implant. Accordingly, tip 14 is inserted through an incision associated with the surgical pocket. As the implant is forced through opening 14, the surgical pocket can be manipulated slightly to create a vacuum that assists in the placement of the implant into the pocket. Additionally, another useful feature of the apparatus and process is that as approximately half of the implant 20 has been exerted through opening 14, the remainder of the implant will flow through the sleeve without additional manipulation. Accordingly, once the opening 14 is positioned within the surgical pocket, implant 20 can be manipulated so that the prosthesis 20 is forced into the surgical pocket. The surgeon is able to control the positioning and orientation of the implant 20 by proper rotation and positioning of the sleeve 10 containing the implant 20.

It has been found that use of a sleeve 10 can greatly reduce the amount of time required for insertion of an implant 20. It has been found that the step of inserting a simple implant can occur within a timeframe of about 3 to 20 seconds minutes as compared to a time interval of 5 to 15 minutes for a traditional hand manipulation of an implant. Additionally, because the implant can be inserted through a small opening, the size of the surgical incision can be made smaller than would otherwise be required for a silicone implant.

The use of the sleeve 10 and implant 20 can be used with incisions. For instance, periareolar, trans axillary, intramammary incisions can be used with the above process and apparatus for insertion of an implant.

In accordance with this invention, it has been found beneficial to initially lubricate the exterior of implant 20 with an appropriate surgical lubricant such as K-Y.RTM. brand sterile lubricant. Following lubrication, the lubricated implant 20 is placed within the sleeve 10 and the implant 20 is forced through opening 14 as a pre-lubrication step. Following this pre-lubrication step, the implant can again be placed within the sleeve and subsequently inserted into the patient's surgical pocket.

It is also envisioned that, depending upon the coefficient of friction of the interior of sleeve 10 and/or any associated liner, it may be possible to provide other types of lubricants, including dry or powdered lubricant products to the interior of sleeve 10. Such lubricants are activated by being moistened and would provide an alternative to manually coating the prosthesis with a lubricant.

If desired, sleeve 10 can further define a structural tip (not illustrated) in association with opening 14. The tip could be provided of a more elastic material that facilitates insertion of the tip into the surgical pocket. For instance, a separate tip could provide for an extension beyond the existing opening 14 and which would have a narrower initial diameter providing a longer tip which may be more easily inserted within the interior of a surgical pocket. The ability of an optional tip to expand allows the implant 20 to pass through sleeve 10 and opening 14 while positioning the exiting implant 20 further within the surgical pocket. The use of the tip is believed beneficial in that it prevents the passage of the implant from extruding the sleeve from the incision. In other words, the tip provides a deeper positioning for the sleeve 10 more accurately directs the placement of the implant within the surgical pocket. The use of an expandable tip may facilitate the insertion time and lessen the learning curve for surgeons who are using the sleeve 10.

An important attribute of sleeve 10, including any optional tip structure 14, is that the interior surface of sleeve 10, including opening 14 and any associated tip member, must provide for a smooth and substantially uninterrupted passageway. It is important that any seams that may be formed or abutments between one type of material to another or from opening 14 to an associated tip must be of a sufficient smoothness such that the surface of the implant 20 is not degraded. Accordingly, it is envisioned that sonically welded seams or the use of a unitary extrusion process is desired for forming appropriate sleeves 10. In addition, to the extent opening 14 may be "cut to size", it is important that the material, once cut, not present any cutting artifacts or roughened edges that could damage the implant 20. Similarly, the identical concerns must be met by any optional tip used with sleeve 10 such that the material of the tip as well as its method of attaching the tip to the sleeve 10 and sleeve opening 14 must not present any potential implant contact surfaces that could result in damage to the implant.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention which is set forth in the following claims. In addition, it should be understood that aspects of the various embodiments may be interchanged, both in whole, or in part. Therefore, the spirit and scope of the appended claims should not be limited to the description of the preferred versions contained therein.

The invention claimed is:

1. A breast implant delivery apparatus for inserting a breast implant into a surgical pocket in a surgical procedure, comprising:
 a flexible sleeve having a proximal opening and a distal opening, the proximal opening being sized to receive a breast implant and being larger than the distal opening, wherein the flexible sleeve comprises a lubrication on the interior of the sleeve and wherein the flexible sleeve is transparent or semi-transparent and can be manually manipulated to force the breast implant along a length of the interior of the flexible sleeve and through the distal opening, and
 wherein the flexible sleeve is sterile for use in the surgical procedure.

2. The breast implant delivery apparatus of claim 1, wherein the flexible sleeve is transparent.

3. The breast implant delivery apparatus of claim 2, wherein the flexible sleeve is tapered from the proximal opening to the distal opening.

4. The breast implant delivery apparatus of claim 2, wherein the proximal opening is at the termination of the apparatus.

5. The breast implant delivery apparatus of claim 2, wherein the flexible sleeve has indicia for cutting the sleeve to a different dimension.

6. The breast implant delivery apparatus of claim 2, further comprising the breast implant.

7. The breast implant delivery apparatus of claim 6, wherein a lubricant is present on an exterior of the breast implant.

8. The breast implant delivery apparatus of claim 6, wherein the breast implant is a pre-filled breast implant.

9. The breast implant delivery apparatus of claim 8, wherein the breast implant is a pre-filled silicone breast implant.

10. The breast implant delivery apparatus of claim 2, further comprising a liner.

11. The breast implant delivery apparatus of claim 2, wherein the flexible sleeve is in a flattened configuration.

12. The breast implant delivery apparatus of claim 1, wherein the flexible sleeve is semi-transparent.

13. The breast implant delivery apparatus of claim 12, wherein the flexible sleeve is tapered from the proximal opening to the distal opening.

14. The breast implant delivery apparatus of claim 12, wherein the proximal opening is at the termination of the apparatus.

15. The breast implant delivery apparatus of claim 12, wherein the flexible sleeve has indicia for cutting the sleeve to a different dimension.

16. The breast implant delivery apparatus of claim 12, further comprising the breast implant.

17. The breast implant delivery apparatus of claim 16, wherein a lubricant is present on an exterior of the breast implant.

18. The breast implant delivery apparatus of claim 16, wherein the breast implant is a pre-filled breast implant.

19. The breast implant delivery apparatus of claim 18, wherein the breast implant is a pre-filled silicone breast implant.

20. The breast implant delivery apparatus of claim 12, further comprising a liner.

21. The breast implant delivery apparatus of claim 12, wherein the flexible sleeve is in a flattened configuration.

* * * * *